US009919082B2

(12) United States Patent
Harder et al.

(10) Patent No.: US 9,919,082 B2
(45) Date of Patent: Mar. 20, 2018

(54) PNEUMOTHORAX MEDICAL TREATMENT DEVICE

(71) Applicant: H&H Medical Corporation, Ordinary, VA (US)

(72) Inventors: Paul Harder, Williamsburg, VA (US); Timothy Coakley, Virginia Beach, VA (US); James Tyler, Cincinnati, OH (US); Mark Sweatman, Landrum, SC (US)

(73) Assignee: H&H Medical Corporation, Ordinary, VA (US)

( * ) Notice: Subject to any disclaimer, the term of this patent is extended or adjusted under 35 U.S.C. 154(b) by 338 days.

(21) Appl. No.: 14/326,711

(22) Filed: Jul. 9, 2014

(65) Prior Publication Data

US 2016/0008524 A1 Jan. 14, 2016

(51) Int. Cl.
*A61M 1/00* (2006.01)
*A61M 39/24* (2006.01)
(Continued)

(52) U.S. Cl.
CPC .......... *A61M 1/008* (2013.01); *A61B 17/3415* (2013.01); *A61B 17/3474* (2013.01);
(Continued)

(58) Field of Classification Search
CPC .............. A61M 1/008; A61M 25/0606; A61M 25/0612; A61M 25/0631; A61M 25/0643;
(Continued)

(56) References Cited

U.S. PATENT DOCUMENTS

| 5,036,860 A | * | 8/1991 | Leigh ................. A61B 10/0275 |
| | | | 600/567 |
| 5,098,388 A | | 3/1992 | Kulkashi et al. |

(Continued)

OTHER PUBLICATIONS

Azevedo, O. C. et al., Evaluation of tests performed to confirm the position of the Veress needle for creation of pneumoperitoneum in selected patients: a prospective clinical trial, Acta Cirúrgica Brasileira vol. 21 (6) pp. 385-391, 2006.

(Continued)

*Primary Examiner* — Adam Marcetich
(74) *Attorney, Agent, or Firm* — Nixon & Vanderhye P.C.

(57) ABSTRACT

The invention provides for an improved medical device used to remove gas and liquid from the plural cavity between the lung and the chest wall in both stationary and mobile applications. The present invention generally comprises a hollow needle with a hollow closed end stylet slidably received in the needle. The stylet is spring-biased to extend out of the needle end as a safety tip but when pressured is moved to a retracted position to allow for insertion through the chest wall. The pressure needed to insert the needle/stylet combination through the chest wall is applied by a housing at the end of the needle which is contoured for easy grip. While not being applied to the chest wall, the stylet comprises a safety tip, which makes the device safe to handle and apply in stationary or mobile applications. Further, the housing includes a one-way valve is configured permit only the passage of air and bodily fluid out of the pleural cavity without a secondary structure needed. The present invention is useful in safely and effectively treating a variety of related conditions including pneumothorax (collapsed lung), tension pneumothorax (collapsed lung pressing on the heart), and pneumohemothorax (collapsed lung with air and bodily fluids in the pleural cavity).

17 Claims, 2 Drawing Sheets

(51) Int. Cl.
*A61M 5/20* (2006.01)
*A61B 17/34* (2006.01)
*A61B 17/00* (2006.01)

(52) U.S. Cl.
CPC .. *A61B 2017/00809* (2013.01); *A61M 1/0031* (2013.01); *A61M 2210/101* (2013.01)

(58) Field of Classification Search
CPC .............. A61M 1/04; A61M 2210/101; A61B 17/3415; A61B 2017/00809; A61B 17/3474; A61B 17/3496; A61B 17/34; A61B 2017/3456; A61B 17/3494; A61B 2090/08021; A61B 2090/0801; A61B 2017/00115; A61B 2017/00455; A61B 90/03
See application file for complete search history.

(56) References Cited

U.S. PATENT DOCUMENTS

| | | | | |
|---|---|---|---|---|
| 5,256,148 A * | 10/1993 | Smith | ............... | A61B 17/3496 604/158 |
| 5,275,611 A * | 1/1994 | Behl | ............... | A61B 17/34 600/585 |
| 5,312,354 A * | 5/1994 | Allen | ............... | A61B 17/3496 600/566 |
| 5,334,159 A | 8/1994 | Turkel | | |
| 5,364,365 A * | 11/1994 | Wortrich | ............ | A61B 17/3496 604/158 |
| 5,374,252 A * | 12/1994 | Banks | ............... | A61B 17/3496 600/567 |
| 5,685,852 A * | 11/1997 | Turkel | ............... | A61B 17/3401 604/159 |
| 5,725,506 A * | 3/1998 | Freeman | ............ | A61B 17/3415 600/579 |
| 5,997,486 A * | 12/1999 | Burek | ............... | A61B 10/0045 600/573 |
| 6,193,692 B1 * | 2/2001 | Harris | ............... | A61B 17/3417 604/158 |
| 6,447,483 B1 | 9/2002 | Steube et al. | | |
| 6,656,160 B1 | 12/2003 | Taylor et al. | | |
| 7,736,336 B2 | 6/2010 | Plishka et al. | | |
| 2004/0260200 A1 | 12/2004 | Morello | | |
| 2006/0052809 A1 * | 3/2006 | Karbowniczek | ..... | A61B 5/1411 606/181 |
| 2006/0074374 A1 * | 4/2006 | Gresham | ............ | A61B 17/3474 604/26 |
| 2006/0253146 A1 * | 11/2006 | Marshall | ............ | A61B 5/15142 606/182 |
| 2007/0142846 A1 * | 6/2007 | Catanese, III | ..... | A61B 17/0469 606/142 |
| 2007/0208271 A1 * | 9/2007 | Voegele | ............ | A61B 10/0275 600/564 |
| 2009/0036915 A1 * | 2/2009 | Karbowniczek | ..... | A61B 5/1411 606/182 |
| 2010/0010468 A1 * | 1/2010 | Becker | ............... | A61M 5/329 604/506 |
| 2011/0112438 A1 * | 5/2011 | Radzuinas | ....... | A61B 5/150022 600/583 |
| 2013/0053828 A1 * | 2/2013 | Hensler | ............... | A61M 1/0041 604/541 |
| 2013/0116710 A1 * | 5/2013 | Ziniti | ............... | A61B 17/0469 606/144 |
| 2014/0046303 A1 * | 2/2014 | Donaldson | ......... | A61B 17/3415 604/540 |

OTHER PUBLICATIONS

Lubin, D. et al., Modified Veress needle decompression of tension pneumothorax: a randomized crossover animal study (Abstract). J Trauma Acute Care Surg. vol. 75 (6) pp. 1071-1075 Dec. 2013.
Novak, M., Winning hearts, minds and saving a young life, The Tribune Democrat Nov. 10, 2009.

* cited by examiner

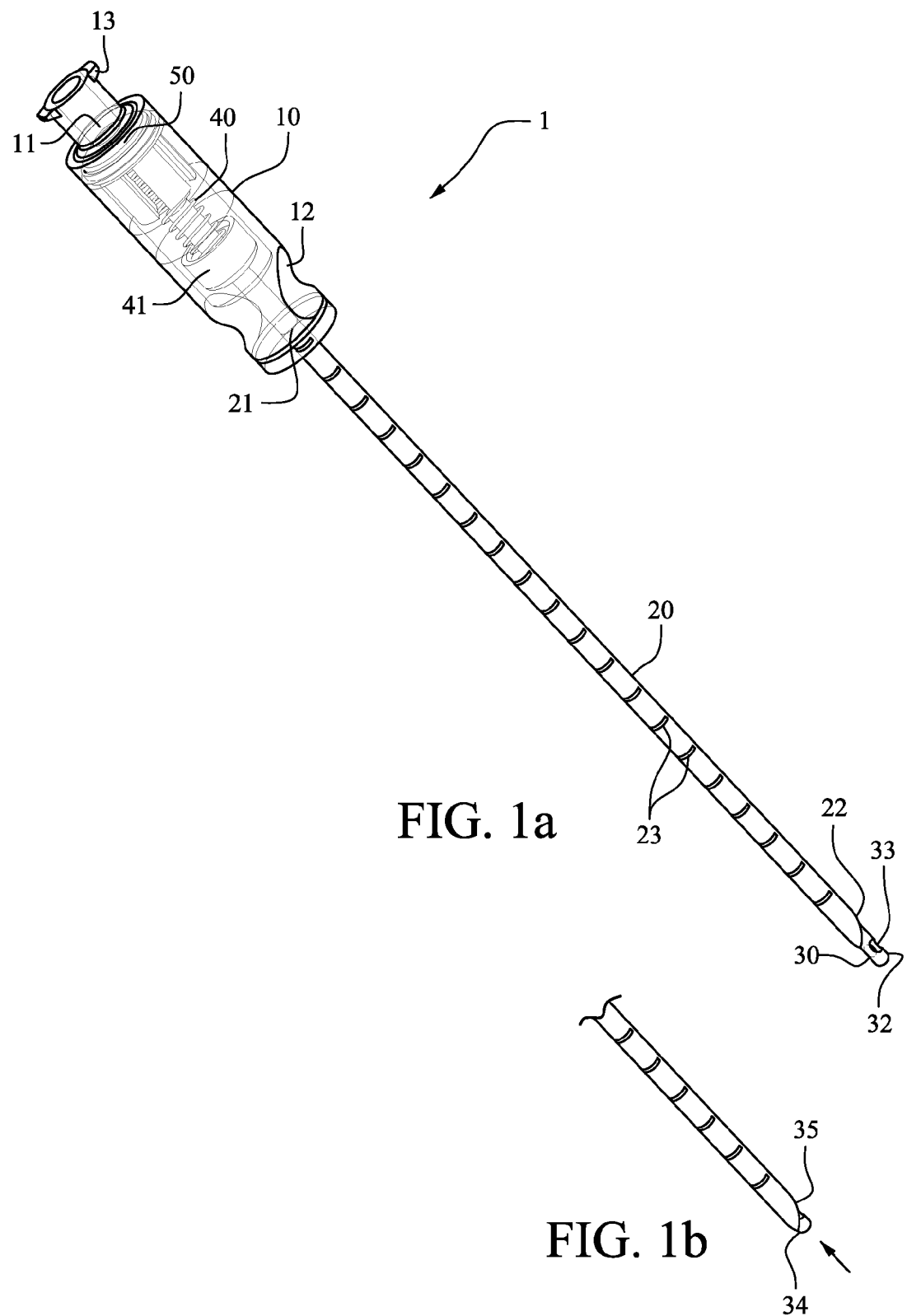

PNEUMOTHORAX MEDICAL TREATMENT DEVICE

BACKGROUND OF THE INVENTION

Field of the Invention

The present invention relates to a medical device used to remove gas and liquid from the plural cavity between the lung and the chest wall. It is useful in treating a variety of related conditions including pneumothorax (collapsed lung), tension pneumothorax (collapsed lung pressing on the heart), and pneumohemothorax (collapsed lung with air and bodily fluids in the pleural cavity).

Discussion of Current Methods

A pneumothorax, tension pneumothorax, or pneumohemothorax is caused by the progressive build-up of air within the pleural space or pleural cavity between the chest wall and the lung and is often a result of a laceration to the lung, which allows air and/or bodily fluids to escape from the lung into the pleural cavity.

In mammals, inhalation causes the chest walls to move up and out and the diaphragm, at the lower portion of the thorax, to depress. The lungs, pushed by atmospheric pressure, expand with air to match the pressure gradient. On exhalation, the chest walls move down and in and the diaphragm rises, squeezing the lungs, forcing air from them through the nose and mouth except in the case of a laceration of the lung. The lungs remain inflated, under normal conditions, because of the slight negative pressure in the plural cavity. However, chest trauma allowing air and/or bodily fluids into the pleural space can raise the pressure of the environment, and subsequently collapse the lung.

During respiration, a build up of air and pressure can occur in the pleural space allowing the collapsed lung to push against the pleural wall and may obstruct venous return of deoxygenated blood to the heart. The eventual result of this obstruction from the tension pneumothorax, or pneumohemothorax may result in decreased heart function or traumatic arrest.

Problems with the cannula inserted by the needle are the difficulty in applying sufficient pressure to force the needle with the external cannula into and through the chest wall. When pressure is applied, even a skilled operator may inadvertently puncture the lung with the needle upon entry into the pleural cavity. This would further compound the build-up of air or fluid into the pleural cavity, nullifying the benefits of the application. Further problems can be created after removal of the insertion needle if the cannula is kinked or twisted so as to restrict the passage through the cannula. Also, the open cannula can easily convey non-sterile air into the pleural cavity.

It is desirable to provide a medical device which mitigates the problems associated with the current methods including those involving a plastic cannula. These problems include ease of insertion, inadvertent entry or laceration of the lung during insertion, prevention of any obstruction of the airway and prevention of non-sterile air entering the pleural cavity.

SUMMARY OF THE INVENTION

The present invention generally comprises a hollow needle with a hollow closed end stylet slidably received in the needle. The stylet is spring-biased to extend out of the needle end as a safety tip but configured to be moved to a retracted position during insertion through the chest wall. The pressure needed to insert the needle/stylet combination through the chest wall is applied by a housing at the end of the needle which is contoured to provide a gripping surface. While not being applied to the chest wall, the stylet comprises a safety tip, which makes the device safe to handle and apply in stationary or mobile applications. Further, the housing includes a one-way valve which is configured without a secondary structure to restrict the passage of air and bodily fluids to only one direction, out of the pleural cavity. There is also an indicator in the housing which shows the extended or retracted position of the stylet in the needle.

One-way valves are known and operate to allow fluid and gas flow in only one direction. A poppet or mushroom valve, as shown in one of the preferred embodiments, is one example of a one-way valve. The portion of the outlet plugged by the valve is known as the seat or the valve seat. In present invention, an application of pressure from inside the housing will cause the valve to lift off of the seat and open allowing fluid to pass out of the housing. Application of pressure from the outside atmosphere will apply a force on the top of the valve, causing the valve to seat over the outlet, closing the valve.

The current methods of treating a pneumothorax are not universally applicable to both on-site and hospital treatments. Operator error is common among the devices currently used, as the force required to puncture the chest wall may lead to further damage to the lung once the needle has reached the extent of the pleural cavity. Devices can also be difficult to secure to the patient without bending and/or kinking because the cannula, tubing or sheath, which is intended to remain inside the patent is small and fits snugly over the puncturing needle, which, to the contrary, is intended to be removed from the patient.

The present invention provides an improved treatment for pneumothorax, tension pneumothorax, and pneumohemothorax; provides a safety mechanism for ease of successful application and safeguards the lung once the device has entered the pleural cavity; provides a visual indication to the operator that after insertion, the stylet has been extended and that the flow between the pleural cavity and the atmosphere is not impeded; provides a device comprising a permanent one-way valve that can be connected to a weak vacuum source; and provides a device, which is relatively simple to manufacture and particularly well adapted for its intended usage.

BRIEF DESCRIPTION OF THE DRAWINGS

Other advantages of this invention are made apparent in the following descriptions taken in conjunction with the provided drawings wherein are set forth, by way of illustration and example, certain exemplary embodiments of the present invention.

FIG. 1a is a perspective view of a first embodiment in the extended position.

FIG. 1b is a perspective view of a first embodiment in the retracted position.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 2A:
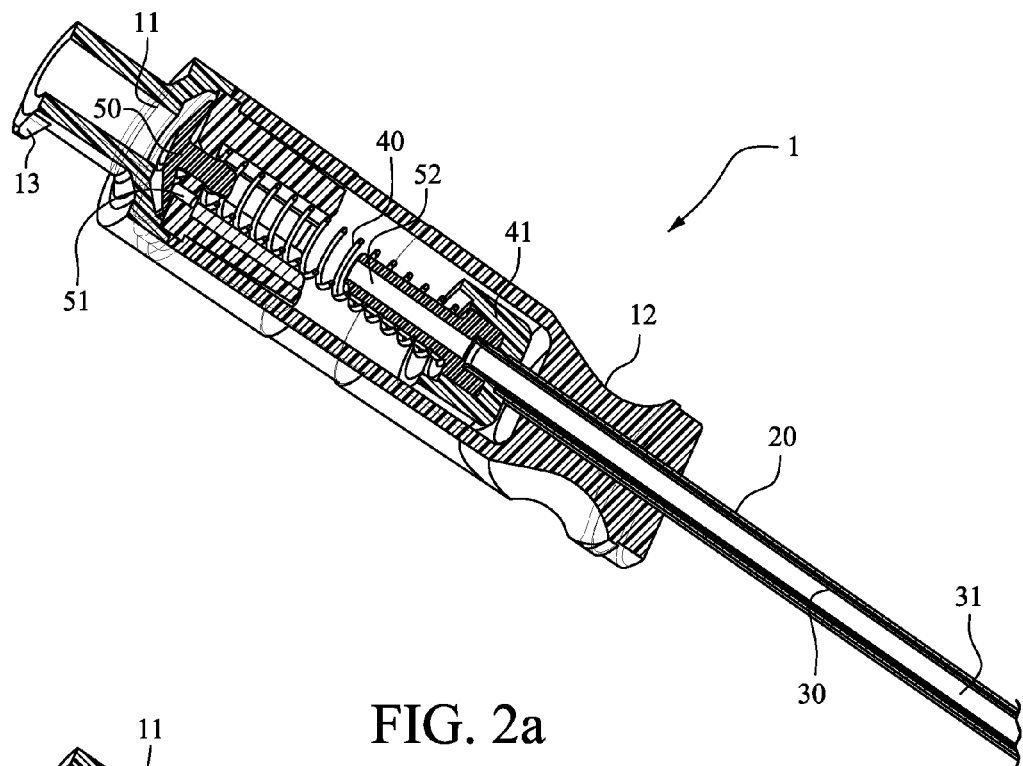
FIG. 2a is a close-up, cross-sectional view of a first embodiment in the extended position.
Figure 2B:
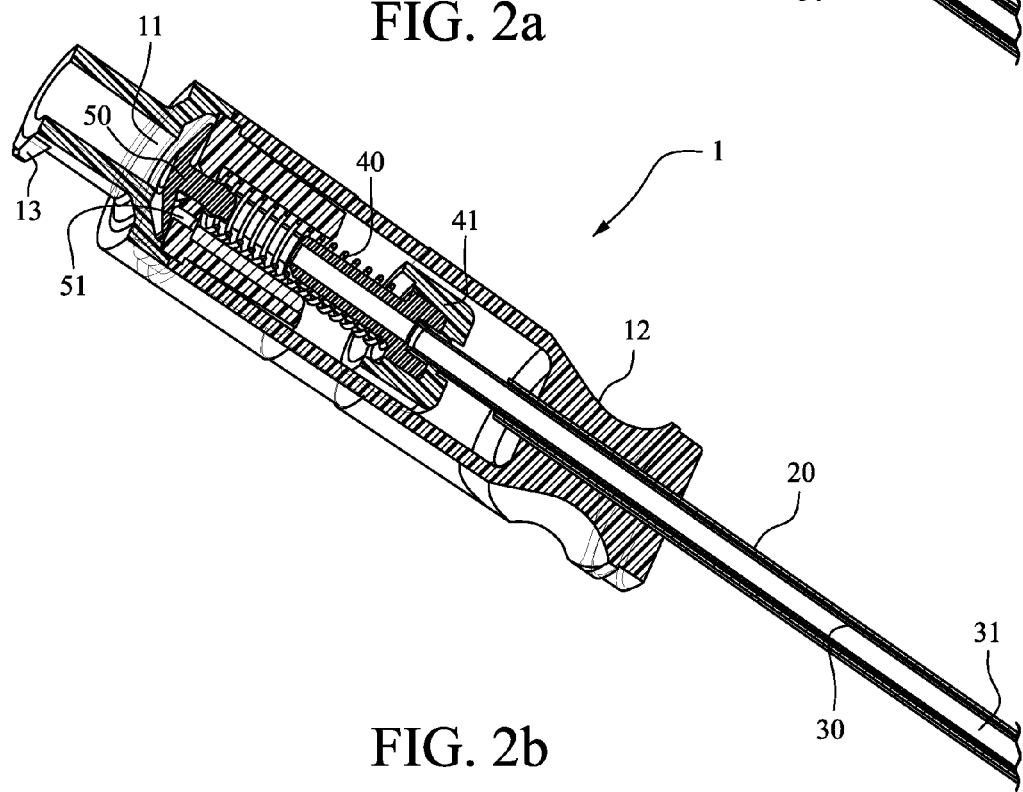
FIG. 2b is a close-up, cross-sectional view of a first embodiment in the retracted position.

As shown in FIGS. 1a through 2b, the device 1 generally comprises: A housing 10 with an outlet 11. A hollow needle 20 with one end 21 secured to said housing 10 opposite said housing outlet 11 and another tapered end 22 extending from said housing. A stylet 30 with a hollow inner passage 31, and is slidably received in said needle and moveable between an extended position, in which a closed end 32 of said stylet extends beyond the tapered end of the needle, and a retracted position, in which the closed end of said stylet does not extend beyond said needle. The stylet includes at least one aperture 33 adjacent the closed end which is fluidly connected to the hollow inner passage. A spring 40 biases the stylet towards said extended position but can be moved by pressure on the tip to the retracted position when the needle is inserted into the chest wall. A one-way valve 50 is located in the housing, and is fluidly connected to said stylet aperture and is configured to only permit flow of gas and/or liquids into the stylet through the aperture and out of the outlet.

The one way valve 50, is fluidly connected to the housing by a passage 51 and fluidly connected to the inner passage 31 of the stylet 30 by a connection 52. When the pressure of gas and/or fluid in passage 51 is greater than the pressure on the top of mushroom valve 50, the valve will at least partially open and allow the gas and/or fluid to flow out of the outlet 11. While in this specific embodiment, a mushroom valve is shown, any valve that restricts flow of gas and/or fluid in a single direction, from said stylet aperture to said housing outlet may be used.

In one embodiment, housing 10 with outlet 11 would be shaped to provide a gripping surface 12 configured to permit an operator to exert a force on needle sufficient to penetrate the chest wall of a patient.

In another embodiment, the housing further comprises a visual indication 41, connected to the stylet, for providing a visual indication at the housing for indicating when the stylet is in the retracted state. Such a visual indication could include, for example, a colored portion of spring, markings to designate extended and retracted position, a lever, a ball and float, etc. The visual indication may also provide a support for the spring 40.

In another embodiment, the hollow needle 20 and the stylet 30 preferably comprise stainless steel. Preferably, the hollow needle 20 and the stylet 30 comprise medical grade material. Preferably, the hollow needle 20 and the stylet 30 and device 1 comprise medical grade material resistant to the temperatures required by sterilization.

In another embodiment, the device further comprises means for fluidly connecting 13 the housing outlet and the one-way valve to any fluid fitting, where the means for connecting includes a stopcock, a Luer lock, a threaded fitting, slip-tips, fluid couplings, ridged tips, tube fittings, quick-connect fittings, adaptors, nozzles, or combinations thereof.

In another embodiment, wherein the outside surface of said stylet 34 and the inside surface of said hollow needle 35 are configured to slide against one another when moving from the retracted and extended position to effectively scrape and clear said outside surface of said stylet.

In another embodiment, the outer surface of said hollow needle has graduations 23 in intervals to allow an operator to determine the depth of penetration of the device to more accurately and effectively treat all sizes of patients.

Current methods for treating a pneumothorax typically involve removing the entrapped air or fluid from the pleural space. An insertion needle with a surrounding plastic cannula is generally forced into the pleural cavity of the patient through a point between the ribs, determined by feel by an operator. The needle can then be removed leaving only the plastic cannula, which can then be secured to the patient. The exposed end of the tubing may also be connected to a slight vacuum source to pull air and fluids out of the pleural cavity and prevent air from re-entering the pleural space.

It is to be understood that while certain forms of the present invention have been illustrated and described herein, it is not to be limited to the specific forms or arrangement of parts described and shown.

The invention claimed is:

1. A medical device for treating tension pneumothorax in a human patient, said device comprising:
   a housing including an outlet, an interior chamber in fluid communication with the outlet and a needle mount in an end of the housing opposite to the outlet,
   a hollow needle including a proximal end and a distal end, the proximal end is seated in and secured to the needle mount of said housing, wherein the hollow needle extends from the housing to the distal end, the distal end is configured to penetrate a chest wall of the human patient and an exposed outer surface of the hollow needle is visible while the hollow needle is inserted into the chest wall,
   a hollow stylet permanently within and coaxial to the hollow needle, wherein the hollow stylet includes a proximal end extending into the interior chamber, a distal portion having a closed end, and an internal passage within the hollow stylet extending from the distal portion to an outlet at the proximal end of the hollow stylet,
   wherein the hollow stylet is slidably received in said hollow needle such that an outer surface of the hollow stylet slides against an inner surface of the hollow needle, and the hollow stylet slides between an extended position at which the closed end of the hollow stylet extends beyond the distal end of said hollow needle, and a retracted position at which the closed end of the hollow stylet is retracted within the hollow needle,
   said hollow stylet including at least one aperture in the distal portion and forming an inlet to the internal passage within the hollow stylet,
   a spring configured to bias said hollow stylet towards said extended position, wherein the spring is within the interior chamber of the housing, between the proximal end of the hollow stylet and the outlet to the housing, and does not overlap with the stylet, and
   a spring support fixed to the proximal end of the stylet and including a passage with an inlet aligned with the proximal end of the stylet and an outlet at an end of the spring in the interior chamber of the housing, wherein the spring support overlaps with the spring and the stylet.

2. The medical device of claim 1, wherein said housing is shaped to provide a gripping surface, said gripping surface of said housing configured to permit an operator to exert a force on said needle sufficient to penetrate a chest wall of said human patient.

3. The medical device of claim 1, further comprising a visual indicator, connected to said stylet, configured to provide a visual indication at said housing indicating when the stylet is in the retracted state, wherein the visual indicator is fixed to the proximal end of the hollow stylet and supporting an end of the spring.

4. The medical device of claim 1, further comprising a one-way valve within the interior chamber of the housing and between the spring and the outlet to the housing, wherein the one-way valve permits gas to flow only from the proximal end of the hollow stylet, through the interior chamber of the housing and towards the outlet.

5. The medical device of claim 1, wherein said hollow needle and said hollow stylet are comprised of stainless steel.

6. The medical device of claim 1, wherein the outer surface of said hollow stylet and the inner surface of said hollow needle are configured to slide against one another while the hollow stylet moves between the retracted and extended positions.

7. The medical device of claim 1, wherein said the at least one aperture in the distal portion of the hollow stylet comprises at least two apertures fluidly connected to the passage in the hollow stylet.

8. The medical device of claim 1, wherein the outer surface of said hollow needle is graduated or marked off in regular intervals from the housing to the distal end of the hollow needle.

9. The medical device of claim 1, further comprising a container, sterilized and vacuum sealed after said medical device is placed inside the container.

10. The medical device of claim 1, wherein said medical device is comprised of parts configured to resist temperatures of sterilization.

11. The medical device of claim 1, wherein said housing is transparent.

12. The medical device of claim 1, wherein an outer diameter of the hollow needle is configured to conform to a size defined by the Birmingham Wire Gauge.

13. The medical device of claim 1, wherein said housing is configured to rest upon the chest wall of the patient, to more easily secure said device to said patient.

14. The medical device of claim 1, wherein said housing is shaped to provide a gripping surface,
wherein said hollow needle and said hollow stylet are comprised of stainless steel,
wherein the outer surface of said hollow stylet and the inner surface of said hollow needle are configured to slide against one another while the hollow stylet moves between the retracted and extended position, and
a visual indicator connected and fixed to said hollow stylet, supporting an end of the spring, and providing a visual indication at said housing indicating when the hollow stylet is in the retracted state.

15. The medical device of claim 1, wherein the spring support includes a stem extending away from the proximal end of the hollow stylet and extend into the spring.

16. A method for treating a tension pneumothorax in a human patient with a medical device comprising:
a housing with an outlet, a mount, and an interior chamber between the outlet and the mount;
a hollow needle including a proximal end secured to the mount of the housing, and a shaft extending from said housing to a distal end, wherein the shaft has an exposed outer surface,
a hollow stylet including an open proximal end, a closed distal end and an interior passage extending from an opening adjacent the closed distal end to the open proximal end that is open to the interior chamber of the housing; and said hollow stylet is slidably received in said hollow needle such that an outer surface of the hollow stylet slides against an inner surface of the hollow needle as the hollow stylet moves between an extended position at which the closed distal end of said hollow stylet extends beyond the distal end of said hollow needle, and a retracted position at which the closed distal end of said stylet is retracted within said hollow needle;
a spring configured to bias said hollow stylet towards said extended position, wherein the spring is within the interior chamber of the housing, between the proximal end of the hollow stylet and the outlet to the housing and does not overlap the hollow stylet; and
a spring support fixed to the proximal end of the stylet and including a passage with an inlet aligned with the proximal end of the stylet and an outlet at an end of the spring in the interior chamber of the housing, wherein the spring support overlaps with the spring and the stylet,
said method comprising:
while grasping the housing, applying a downward pressure to the closed end of said stylet to temporarily overcome said spring bias and move said stylet into said retracted position,
continuing said application of pressure as said distal end of said hollow needle passes through the chest wall and continuing the application of pressure only until said distal end enters the pleural cavity of said patient, and
monitoring a depth of the insertion of the hollow needle into the chest by visually inspecting the outer surface of the hollow needle.

17. The method of claim 16 further comprising applying a vacuum to said housing outlet.

* * * * *